United States Patent
Fadem et al.

(10) Patent No.: US 6,254,533 B1
(45) Date of Patent: Jul. 3, 2001

(54) RETRACTOR ASSEMBLY AND METHOD FOR SURGICAL PROCEDURES

(75) Inventors: Kalford C. Fadem, Atlanta, GA (US); Frederic C. Feiler, Jr., Raleigh, NC (US)

(73) Assignee: Dexterity Surgical, Inc., Roswell, GA (US)

( * ) Notice: Subject to any disclaimer, the term of this patent is extended or adjusted under 35 U.S.C. 154(b) by 0 days.

(21) Appl. No.: 09/611,453

(22) Filed: Jul. 7, 2000

(51) Int. Cl.[7] ........................................... A61B 1/32
(52) U.S. Cl. .......................... 600/208; 600/233; 600/231
(58) Field of Search ..................................... 600/184, 201, 600/206, 207, 208, 227, 231, 233; 128/850; 606/213

(56) References Cited

U.S. PATENT DOCUMENTS

| | | | |
|---|---|---|---|
| 1,157,202 | * 10/1915 | McLeland | 600/233 X |
| 5,480,410 | * 1/1996 | Cuschieri et al. | 606/213 |
| 5,520,610 | * 5/1996 | Giglio et al. | 600/233 |
| 5,649,550 | * 7/1997 | Crook . | |
| 5,813,409 | * 9/1998 | Leahy et al. | 128/897 |
| 5,906,577 | * 5/1999 | Beane et al. | 600/207 |
| 6,033,426 | * 3/2000 | Kaji | 600/207 X |

\* cited by examiner

*Primary Examiner*—Jeffrey A. Smith
(74) *Attorney, Agent, or Firm*—Don Halgren

(57) ABSTRACT

The present invention covers a surgical wound protector apparatus for the protective support of an incision and support of surgical apparatus utilized within the incision. The apparatus comprises a flexible resilient wound liner sleeve having an open upper end and an open lower end with a rigid annular ring arranged to securely receive the upper end of the resilient sleeve when the sleeve and the ring are applied to an incision of a patient.

17 Claims, 4 Drawing Sheets

RETRACTOR ASSEMBLY AND METHOD FOR SURGICAL PROCEDURES

BACKGROUND OF THE INVENTION

1. Field of the Invention

This invention relates to retractors and more particularly to surgical incision protectors and internal body organ retraction arrangements which permit an operating surgeon proper open surgical access to the surgical site.

2. Prior Art

Incisions made during surgical procedures require sterility of the operating field, maintenance of the incision or wound site against malignant or infectious contamination and peripheral retraction to provide a maximum circular exposure as possible with a minimum incision size. Retraction of various body organs out of the way of the surgeon, the surgical tools and the tissue being treated, is also a consideration during any surgical procedure. Retractors which attempt to do this have been around for a long time. Such retractors may be exemplified by U.S. Pat. No. 1,839,726 to Arnold, showing a circular ring with a plurality of clamps mounted thereon. Such retractors are typically attached to the table on which the patient is lying. The actual blades which comprise the retractors are typically supported by long arms attached to the retractor ring. Such a structure is cumbersome and minimizes the ability of the surgical team to readily move about. Such arrangements are typical even to this day, as may be seen in U.S. Pat. No. 5,520,610 to Giglio et al.

The incision itself, as aforementioned, is desirably protected by an incision liner and retractor, as may be seen in U.S. Pat. No. 5,524,644 to Crook and incorporated herein by reference. Such a "sleeve-like" liner and retractor is arranged to fit within the incision, having an O-ring along a lowermost peripheral edge, and a further, somewhat more flexible O-ring along its uppermost peripheral edge of the annular liner. The liner is adjustable by virtue of its being able to be rolled-up about its uppermost O-ring, so as to snuggly engage and hence protect the periphery of the incision. A further retractor and liner is shown in U.S. Pat. No. 5,649,550 to Crook, and incorporated herein by reference, which patent discloses a drape assembly, which is integral with the liner. The O-rings on such a retractor arrangement must of necessity be flexible so as to be folded or bent, so as to be inserted within the incision. The upper O-ring must be flexible and resilient enough so as to permit the sleeve material to be rolled-up about the upper O-ring once the sleeve is to be joined against the incision walls. The retraction force of the O-rings, and particularly the upper O-ring, in certain instances, is insufficient to support retractor blades or provide maximum incision retraction. Also, such a retractor does not provide retraction for internal organs.

It is an object of the present invention, to improve upon the retractor assemblies of the prior art.

It is a further object of the present invention, to provide a retractor assembly that protects the wound or incision periphery while also permitting the attachment of blade retractors into the surgical site of the patient.

It is still yet a further object of the present invention to provide an apparatus which will provide rigidity to the uppermost end of a flexible sleeve mated within an incision, while also providing a platform for the suspension of surgical tools and wound treatment apparatus.

BRIEF SUMMARY OF THE INVENTION

The present invention comprises an adjustable surgical wound protector and incision retractor (protractor) and stiffener ring support arrangement. The protractor comprises a flexible sleeve of thin material, impervious to solids or fluids containing bacteria and other contaminants. The flexible sleeve has an opening at each opposed end thereof, having a first or a lower O-ring at a first end, and a second or upper O-ring at its second end. The portion of the sleeve extending above the wound incision is rolled about the upper or second O-ring, to reduce the longitudinal dimension of the sleeve into a tight contiguous engagement with the sides of the wound incision.

In the first preferred embodiment of the present invention, a protractor stiffening ring is placed about the wound periphery, according to the size of the particular incision. The rolled-up uppermost portion of the protractor sleeve is inserted within a channel of the protractor stiffening ring. The protractor stiffening ring comprises an inner flange, a base portion, and an outer flange, which defines the channel into which the rolled-up outer ring is inserted. The channel thus may comprise an interrupted or continuous annular trough defining the periphery of the surgical site. A lip extends radially outwardly from the uppermost edge of the outer flange, to define a support surface for a movable blade-receiving adapter. The peripheral lip has a peripheral edge on its outermost side having a plurality of notches thereon. The movable blade adapter comprises a cylindrically-shaped housing for receipt of a portion of a paddle or blade arm. The paddle or blade arm extends within the opening of the incision on the radially inside of the sleeve. The blade arm has an elbow portion which extends through the movable blade adapter, for engagement therewithin. The adapter has an innermost lip and an outermost tab, for secure engagement within the notches on the peripheral edge of the lip base. Thus, once the protractor sleeve is fully wound up and snuggly engaged within the channel of the protractor stiffening ring, one or more movable blade adapters may be secured to the top side of the stiffening ring, and retractor blades or paddles may be juxtaposed therewithin to hold body organs out of the way of the surgical procedure during the treatment of the patient.

A further embodiment shows an L-shaped retractor ring defined by an annular base having an inner flange extending upwardly therefrom. A blade support station may be arranged at various spaced-apart locations about the periphery of the annular base of the L-shaped protractor ring. The upper end of each blade support station has an opening therethrough in radial alignment with the longitudinal axis of the sleeve about which it is disposed. A retractor blade or paddle, is arranged within the sleeve, and has an uppermost arm and elbow portion which extend s through the opening of each blade support station. The sleeve and O-ring, are mated above and below the incision in the patient's abdomen as in the aforementioned embodiment. The sleeve is wound up above about the uppermost O-ring as in the aforementioned embodiment, the wound-up sleeve and upper O-ring mating in with the space between the blade support stantions and the inner flange of the annular base. Frictional engagement between the blade support stantions and the inner flange provides the tautness of the sleeve. The retractor ring provides the stiffness, as in the aforementioned embodiment, to the assembly, for support of the retractor blades and the paddles in a circular pattern about the edge of the incision.

In yet a further embodiment of the stiffening ring, an L-shaped base and flange ring is arranged so as to fit about the periphery of an incision or wound site in a generally circular manner. The upper end of the sleeve and upper O-ring is rolled and fitted into the corner of the L-shaped ring for retention thereof and maintenance of the generally circular configuration of the sleeve and incision of the wound site.

A further embodiment of the retractor arrangement of the present invention comprises the annular stiffener ring having an annular base portion, similar to the aforementioned embodiment. However, a flexible resilient torroidally shaped chamber is attached to the lower side of the annular base. This torriodally shaped chamber provides an airtight fit between the stiffening ring and the peripheral surface of the abdomen incision about which the retainer ring is placed. The torroidally-shaped chamber may be filled with a resilient material or pressurizably actuated by a fluid pumnpable therewithin.

The outermost flange may have a notch circumferentially spaced around its outermost surface, so as to receive an O-ring for sealing purposes. A cover or dome m ay be arranged so as to snap over the outermost flange of the stiffener ring to provide containment, security and cleanliness for the surgical site. The cover or dome may have an instrument opening therein, to permit laparoscopic surgical procedures to be performed within that site. The stiffener ring in this embodiment also contains an annular trough, as in the earlier embodiment, so as to permit the first or uppermost end of a sleeve to be rolled up and inserted within that channel.

Thus what has been shown are a number of embodiments of stiffener rings, to provide an oddity to a protractor sleeve so as to both protect the periphery of the incision or wound site as well as to provide a base for support of retractor blades or paddles to hold organs in place or aside during a particular surgical procedure.

The invention thus comprises a surgical wound protector apparatus for the protective support of an incision and support of surgical apparatus utilized within the incision, comprising: a flexible resilient wound liner sleeve having an open upper end and an open lower end; and a rigid annular ring arranged to securely receive the upper end of the resilient sleeve when the sleeve the ring are applied to an incision of a patient. The ring includes a channel for receipt of said upper end of said sleeve. A retractor blade and arm may be attached to the annular ring. The channel has a retractor blade arm receiver arranged thereon to controllably support the blade thereon when the apparatus in placed about an incision. The rigid annular ring comprises an annular base and an inner upstanding flange. The rigid annular ring also comprises an outer upstanding flange, extending from the annular base. The inner upstanding flange has a securement lip extending radially outwardly from an upper edge thereof. A resilient torroidally shaped chamber may be attached to a lower side of the rigid annular ring to function as a sealant between a wound site of a patient and the rigid ring. A dome shaped cover may be arranged to mate onto a flange of the rigid ring. The rigid ring may include a second flange. The cover has an annular rim, the flange and the annular rim having an O-ring sealingly arranged therebetween. The dome may have a sealable port thereon to permit access of surgical apparatus therethrough. The chamber on a lower side of the ring may be pressurized.

The invention also includes a method of supportively protecting a surgical incision comprising the steps of: placing a resilient wound protecting protractor sleeve within the surgical incision; arranging a rigid ring around the surgical incision, the ring having an annular base and a flange upstanding therefrom; rolling-up an upper end of the sleeve so as to tightly engage the incision by the sleeve; and placing the rolled-up portion of the sleeve securely onto the rigid ring for maintenance of the sleeve about the incision. The method may include one or more of the steps of: arranging a retractor blade arm receiver onto the rigid ring; attaching a retractor blade to the receiver on rigid ring to permit the blade to support and maintain body tissue in the patient being treated; placing a dome cover onto the flange of the ring to enclose the wound site of the patient; arranging a sealably openable port in the dome to permit controlled access to the incision site on the patient; attaching a pressurized torroidally shaped chamber onto a lower side of the ring to sealing mate the ring to a patient being treated.

BRIEF DESCRIPTION OF THE DRAWINGS

The objects and advantages of the present invention will become more apparent, when viewed in conjunction with the following drawings in which.

DESCRIPTION OF THE PREFERRED EMBODIMENTS

Figure 1:
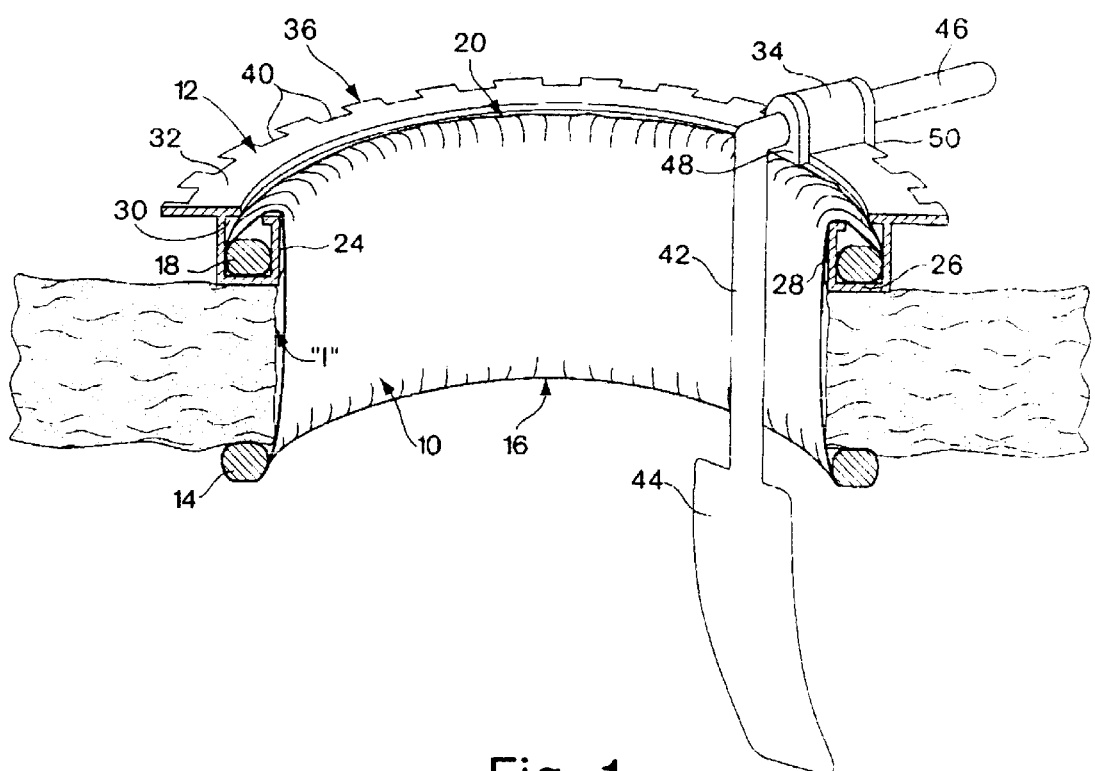
FIG. 1 is a side elevational view, in section, of a wound incision protective sleeve arranged within a stiffener ring at its uppermost end, and a retractor arrangement associated therewith.

Referring now to the drawings in detail, and particularly to FIG. 1, there is shown a preferred embodiment of the present invention which comprises an adjustable surgical wound protector/incision retractor (protractor) 10 and stiffener ring support arrangement 12. The protractor 10 comprises a flexible sleeve of thin material, impervious to solids or fluids containing bacteria and other contaminants. The flexible sleeve of the protractor 10 has an opening at each opposed end thereof, having a first or a lower O-ring 14 at a first end 16, and a second or upper O-ring 18 at its second end 20. The portion of the protractor sleeve 10 extending above the wound incision "I" is rolled about the upper or second O-ring 18, to reduce the longitudinal dimension of the sleeve into a tight contiguous engagement with the sides of the wound incision "I".

In the first preferred embodiment of the present invention, a protractor stiffening ring 12 is placed about the wound periphery, according to the size of the particular incision "I", as may be seen in FIG. 1. The rolled-up uppermost portion 20 of the protractor sleeve 10 is inserted within a channel 22 of the protractor stiffening ring 12. The protractor stiffening ring 12 comprises an inner flange 24, a base portion 26, and an outer flange 28, which defines the channel 30 into which the rolled-up outer ring 18 and sleeve 10 is inserted. The channel 30 thus comprises an annular trough defining the periphery of the surgical site. A lip 32 extends radially outwardly from the uppermost edge of the outer flange 28, as shown in FIG. 1, to define a support surface for a movable blade-receiving adapter 34. The peripheral lip 32 has a peripheral edge 36 on its outermost side having a plurality of notches 40 thereon. The movable blade-receiving adapter 34 comprises a cylindrically-shaped housing for receipt of a portion of a paddle or blade arm 42. The paddle or blade arm 42 has a lower end 44 which extends within the opening of the incision "I" on the radially inside of the protractor sleeve 10. The blade arm 42 has an elbow portion 46 which extends through a bore the movable blade adapter 34, for engagement therewithin. The adapter 34 has an innermost lip 48 and an outermost tab 50, for secure engagement within the notches 40 on the peripheral edge 36 of the lip 32. Thus, once the protractors level 10 is fully wound up and snuggly engaged within the channel 30 of the protractor stiffening, ring 12, one or more movable blade adapters 34 may be secured to the top side of the stiffening ringer 12, and retractor blades or paddles 44 may be juxtaposed therewithin to hold body organs out of the way of the surgical procedure during the treatment of the patient.

Figure 2:
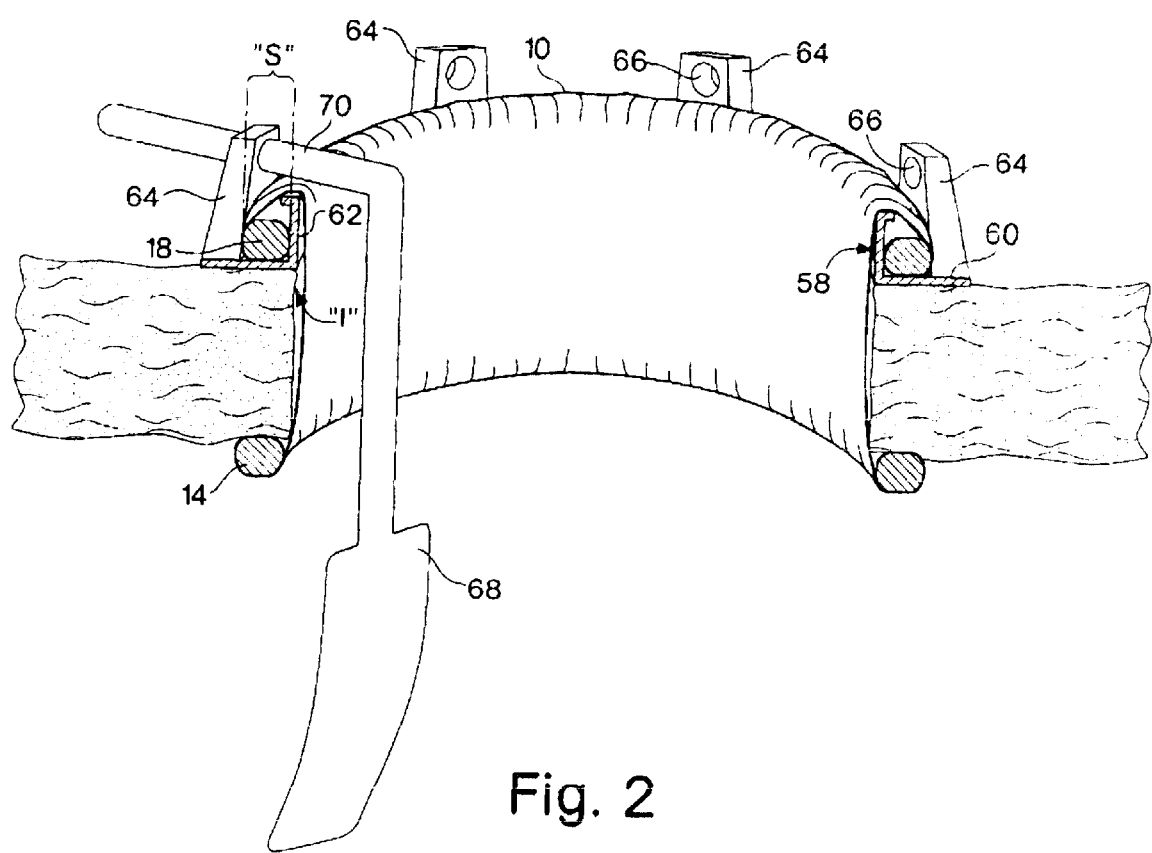
FIG. 2 is a view similar to that shown in FIG. 1 with a further arrangement of retractor blade or paddle support members arranged thereabout.

A further embodiment shown in FIG. 2 discloses an L-shaped retractor ring 58 defined by an annular base 60, having an inner flange 62 extending upwardly therefrom. A blade support station 64 may be arranged at various spaced-apart (i.e. approx. 30 degree) locations about the periphery of the annular base 60 of the L-shaped protractor ring 58, as may be seen in FIG. 2. The upper end of each blade support station 64 has an opening 66 therethrough, in radial alignment with the longitudinal axis of the protractor sleeve 10 about which it is disposed. A retractor blade or paddle 68 is arranged within the sleeve 10, and may have an uppermost arm and elbow portion 70 which extends through the opening 66 of each lade support station 64. The sleeve 10 and lower O-ring 18 are mated adjacent and below the incision "I" in the patient's abdomen as in the aforementioned embodiment. The sleeve 10 is wound up above about the uppermost 0-ring 18 as in the aforementioned embodiment, the wound-up sleeve 10 and upper O-ring 18 mating in with the space "S" between the blade support stantions 64 and the inner flange 62 of the annular base 60. Frictional engagement between the blade support stantions 64 and the inner flange 62 provides the tautness of the sleeve 10. The retractor ring 58 provides the stiffness, as in the aforementioned embodiment, to the assembly, for support of the retractor blades and the paddles 68 in a circular pattern about the edge of the incision "I".

Figure 3A:
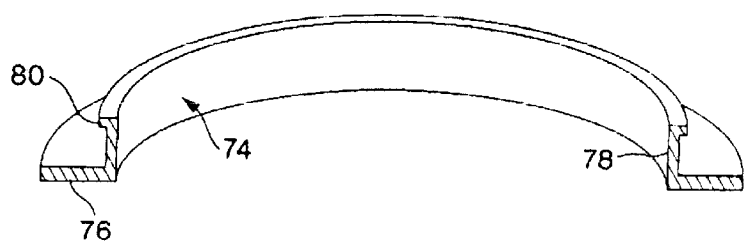
FIG. 3A is a side-elevational view, in section, of a simple stiffening ring for a flexible sleeve protractor.
Figure 3B:
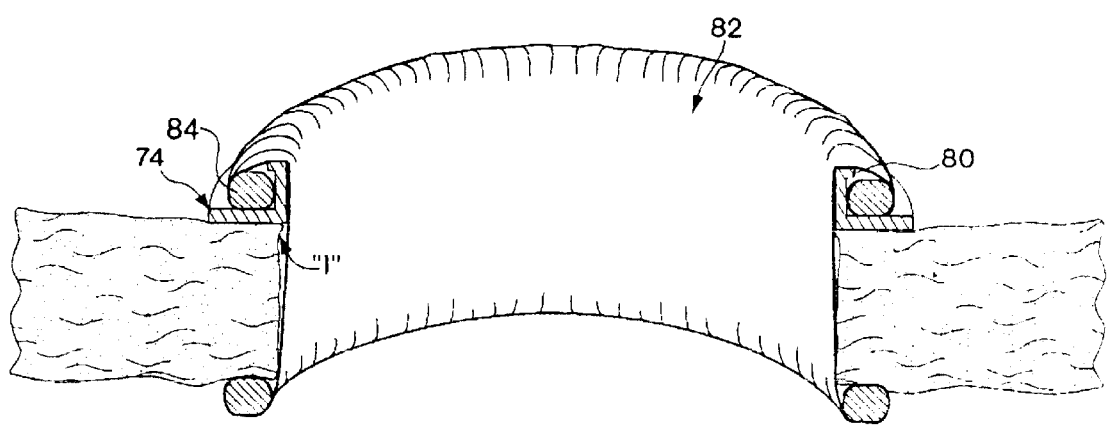
FIG. 3B is a view of the protractor stiffening ring shown in FIG. 3A with a protractor sleeve arranged about a portion of a wound site.
Figure 4:
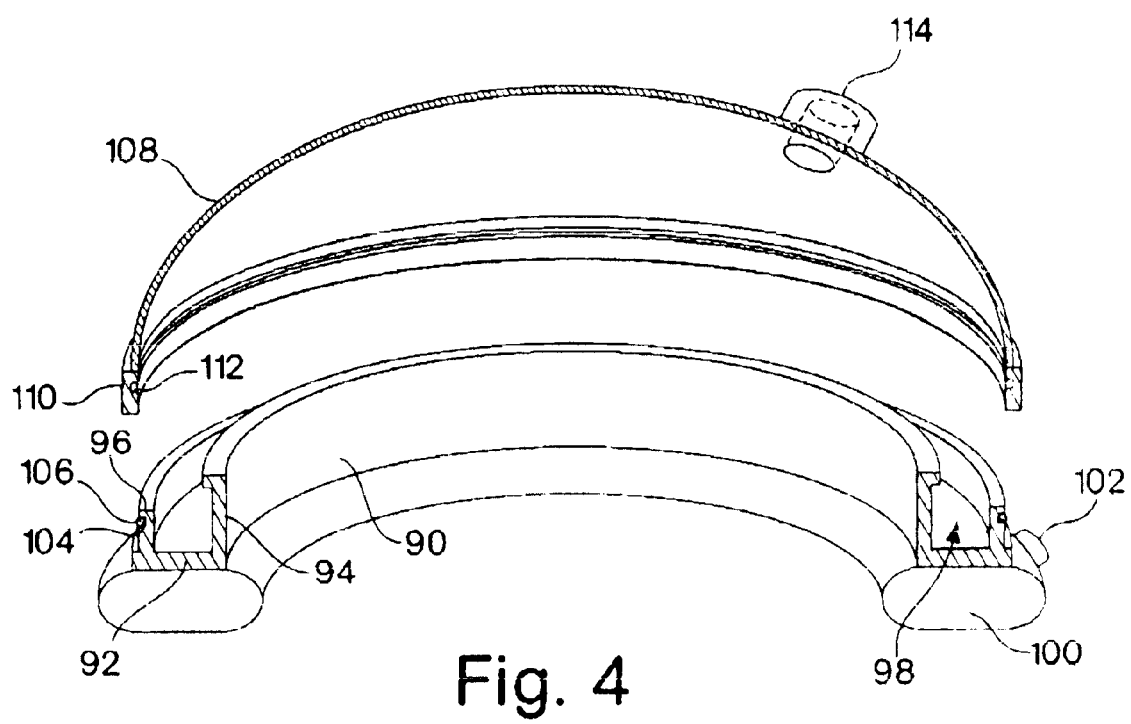
FIG. 4 is an exploded side-elevational view, in section, of a further embodiment of a stiffening ring having further patient assisting devices therewith.

A further embodiment of the stiffening ring 74, is shown in FIG. 3A. The stiffening ring 74 comprises an "L-shaped" combination of an annular base 76 with an upstanding flange ring 78. The flange ring 78 has an upper lip 80 to act as an anti-slip guard. The ring 74 is arranged so as to fit about the periphery of an incision "I" or wound site in a generally circular manner, as shown in combination with a protractor sleeve 82 in FIG. 3B. The upper end of the sleeve 82 has an upper O-ring 84 which is rolled-up in the sleeve 82 and fitted over the lip 80 and into the corner of the L-shaped ring 74 for retention thereof and maintenance of the generally circular configuration of the sleeve 82 and incision "I" of the wound site.

A further embodiment of the retractor arrangement of the present invention comprises the annular stiffener protractor ring 90 having an annular base portion 92, similar to the aforementioned embodiment, with an inner upstanding flange wall 94 and an outer upstanding flange wall 96. An annular channel 98 therebetween defines the trough for securing a rolled-up sleeve, not shown. A flexible resilient torroidally shaped chamber 100 may be attached to the lower side of the annular base 92. This torroidally shaped chamber 100 provides an airtight fit between the stiffener ring 90 and the peripheral surface of the abdomen incision "I" about which the stiffener retainer ring 90 is placed. The to noidally-shaped chamber 100 may be filled with a resilient material or pressurizably actuated by a fluid fill conduit 102.

The outermost flange 96 may have a notch 104 circumferentially spaced around its outermost surface, so as to receive an O-ring 106 for sealing purposes. A cover or dome 108 may be arranged so as to snap over the outermost flange 96 of the stiffener ring 90 to provide containment, pressure, security and cleanliness for the surgical site. The cover or dome 108 has a peripheral lip 10 and corresponding groove 112 to engage the O-ring 106 on the outer flange 96. The cover 108 may have a sealable instrument opening 114 therein, to permit laparoscopic instruments and or treatment arrangements or a surgeon's hand(s) to be disposed through the opening 114 to allow surgical procedures to be enclosively performed within that site.

Thus what has been shown are a number of embodiments of stiffener rings, to provide rigidity to a protractor sleeve so as to both protect the periphery of the incision or wound site as well as to provide a base for support of retractor blades or paddles to hold organs in place or aside during a particular surgical procedure.

We claim:

1. A surgical wound protector apparatus for the protective support of an incision and support of surgical apparatus utilized within the incision, comprising:
    a flexible resilient wound liner sleeve having an open upper end and an open lower end; and
    a rigid annular ring including a channel arranged to securely receive said upper end of said resilient sleeve when said sleeve and said ring are applied to an incision of a patient, said rigid annular ring having a retractor blade and arm attached thereon for assistance during a surgical procedure.

2. The surgical wound protector apparatus as recited in claim 1, wherein said channel has a retractor blade arm receiver arranged thereon to controllably support said blade thereon when said apparatus in placed about an incision.

3. The surgical wound protector apparatus as recited in claim 1, wherein said rigid annular ring comprises an annular base and an inner upstanding flange.

4. The surgical wound protector apparatus as recited in claim 3, wherein said rigid annular ring also comprises an outer upstanding flange, extending from said annular base.

5. The surgical wound protector apparatus as recited in claims 3, wherein said inner upstanding flange has a securement lip extending radially outwardly from an upper edge thereof.

6. The surgical wound protector apparatus as recited in claim 1, including a resilient torroidally shaped chamber attached to a lower side of said rigid annular ring to function as a sealant between a wound site of a patient and said rigid ring.

7. The surgical wound protector apparatus as recited in claim 6, wherein said chamber on a lower side of said ring is pressurized.

8. The surgical wound protector apparatus as recited in claim 1, including a dome shaped cover arranged to mate onto a flange of said rigid ring.

9. The surgical wound protector apparatus as recited in claim 8, wherein said rigid ring includes a second flange.

10. The surgical wound protector apparatus as recited in claim 8, wherein said cover has an annular rim, said flange and said annular rim having an O-ring sealingly arranged therebetween.

11. The surgical wound protector apparatus as recited in claim 8, wherein said cover has a sealable port thereon to permit access of surgical apparatus therethrough.

12. A method of supportively protecting a surgical incision comprising the steps of:

placing a resilient wound protecting protractor sleeve within the surgical incision;

arranging a rigid ring around said surgical incision, said ring having an annular base and a flange upstanding therefrom;

rolling-up an upper end of said sleeve so as to tightly engage said incision by said sleeve; and placing said rolled-up portion of said sleeve securely onto said rigid ring for maintenance of said sleeve about said incision.

13. The method of supportively protecting a surgical incision as recited in claim 12, including the step of:

arranging a retractor blade arm receiver onto said rigid ring.

14. The method of supportively protecting a surgical incision as recited in claim 13, including the step of:

attaching a retractor blade to said receiver on said rigid ring to permit said blade to support and maintain body tissue in the patient being treated.

15. The method of supportively protecting a surgical incision as recited in claim 12, including the step of:

placing a dome cover onto said flange of said ring to enclose said wound site of the patient.

16. The method of supportively protecting a surgical incision as recited in claim 15, including the step of:

arranging a sealably openable port in said dome to permit controlled access to said incision site on said patient.

17. The method of supportively protecting a surgical incision as recited in claim 12, including the step of:

attaching a pressurized torroidally shaped chamber onto a lower side of said ring to sealing mate said ring to a patient being treated.

\* \* \* \* \*